US008706288B2

(12) United States Patent
Alpay

(10) Patent No.: US 8,706,288 B2
(45) Date of Patent: Apr. 22, 2014

(54) APPARATUS AND METHOD FOR NON-CONTACT SENSING OF TRANSPARENT ARTICLES

(75) Inventor: Mehmet Emin Alpay, Portland, OR (US)

(73) Assignee: Electro Scientific Industries, Inc., Portland, OR (US)

( * ) Notice: Subject to any disclaimer, the term of this patent is extended or adjusted under 35 U.S.C. 154(b) by 461 days.

(21) Appl. No.: 12/783,429

(22) Filed: May 19, 2010

(65) Prior Publication Data

US 2010/0298964 A1    Nov. 25, 2010

Related U.S. Application Data

(60) Provisional application No. 61/180,245, filed on May 21, 2009.

(51) Int. Cl.
*G06F 19/00* (2011.01)

(52) U.S. Cl.
USPC .............................. 700/166; 700/114; 702/159

(58) Field of Classification Search
USPC ............ 700/114, 266, 108, 166; 219/121.67, 219/121.68, 121.69; 65/17.1, 29.12, 60.1; 702/158, 159
See application file for complete search history.

(56) References Cited

U.S. PATENT DOCUMENTS

| 4,591,271 | A | 5/1986 | Byers |
| 5,609,284 | A | 3/1997 | Kondratenlo et al. |
| 5,665,134 | A | 9/1997 | Kirby et al. |
| 5,728,994 | A * | 3/1998 | Hutton ..................... 219/121.69 |
| 6,144,010 | A * | 11/2000 | Tsunemi et al. ......... 219/121.68 |
| 6,521,862 | B1 | 2/2003 | Brannon |
| 6,559,411 | B2 * | 5/2003 | Borgeson et al. ........ 219/121.69 |
| 6,720,567 | B2 * | 4/2004 | Fordahl et al. ........... 250/559.29 |
| 6,756,563 | B2 | 6/2004 | Gross et al. |
| 6,778,874 | B2 * | 8/2004 | Schauer ....................... 700/112 |
| 6,992,026 | B2 | 1/2006 | Fukuyo et al. |
| 7,007,512 | B2 | 3/2006 | Kamada et al. |
| 7,023,001 | B2 | 4/2006 | Cournoyer et al. |
| 7,217,448 | B2 | 5/2007 | Koyo et al. |
| 7,267,436 | B2 * | 9/2007 | Ito et al. ................... 219/121.68 |
| 2002/0005805 | A1 | 1/2002 | Ogura et al. |
| 2003/0054107 | A1 * | 3/2003 | Trabold et al. ................ 427/355 |
| 2003/0096078 | A1 | 5/2003 | Horisaka et al. |
| 2003/0150839 | A1 | 8/2003 | Kobayashi et al. |
| 2003/0201261 | A1 | 10/2003 | Kang et al. |

(Continued)

FOREIGN PATENT DOCUMENTS

CN    1813214 A    8/2006
JP    04-348206 A    12/1992

(Continued)

OTHER PUBLICATIONS

International Preliminary Report of PCT/US2010/035811, 4 pages.

(Continued)

*Primary Examiner* — Charles Kasenge

(57) ABSTRACT

A laser-based displacement detector is used to detect cosmetic coatings applied to one surface of the transparent article and thereby determine which side is uppermost when loaded into the laser processing system. In particular, articles that are transparent to visible light and are particularly difficult to orient properly in laser processing systems are oriented using a laser-based displacement detector in conjunction with a partial coating on the article.

20 Claims, 3 Drawing Sheets

(56) References Cited

U.S. PATENT DOCUMENTS

| | | |
|---|---|---|
| 2003/0217568 A1 | 11/2003 | Koyo et al. |
| 2004/0033316 A1* | 2/2004 | Carbonell et al. ......... 427/430.1 |
| 2004/0104846 A1 | 6/2004 | Ogura et al. |
| 2004/0200067 A1 | 10/2004 | Ogura et al. |
| 2005/0184035 A1 | 8/2005 | Kurosawa et al. |
| 2005/0223744 A1 | 10/2005 | Horisaka et al. |
| 2006/0023214 A1 | 2/2006 | Lof et al. |
| 2006/0054843 A1* | 3/2006 | Simpson et al. ......... 250/559.27 |
| 2006/0092990 A1* | 5/2006 | Koga et al. ......................... 372/7 |
| 2006/0127640 A1 | 6/2006 | Kobayashi et al. |
| 2006/0151450 A1 | 7/2006 | You et al. |
| 2007/0039932 A1 | 2/2007 | Haase et al. |
| 2007/0084837 A1* | 4/2007 | Kosmowski ............. 219/121.68 |
| 2007/0170162 A1 | 7/2007 | Haupt et al. |
| 2008/0047933 A1 | 2/2008 | Salminen et al. |
| 2009/0004763 A1* | 1/2009 | Ono et al. ........................ 438/7 |
| 2010/0147813 A1 | 6/2010 | Lei et al. |

FOREIGN PATENT DOCUMENTS

| | | |
|---|---|---|
| JP | 10-221170 A | 8/1998 |
| JP | 2000-061667 A | 2/2000 |
| JP | 2001-033385 A | 2/2001 |
| JP | 2002-122711 A | 4/2002 |
| JP | 2005-049259 A | 2/2005 |
| JP | 2007178367 A | 7/2007 |
| JP | 2009-025995 A | 2/2009 |

OTHER PUBLICATIONS

Oct. 8, 2013 Office Action concerning corresponding Japanese Patent Application No. 2012-512065 (This Office Action was translated and sent to applicant on Oct. 28, 2013).

Oct. 10, 2013 Office Action concerning corresponding Chinese Paten Application No. 201080021456.6 (This Office Action was translated and sent to applicant on Nov. 19, 2013).

* cited by examiner

APPARATUS AND METHOD FOR NON-CONTACT SENSING OF TRANSPARENT ARTICLES

TECHNICAL FIELD

This application claims priority from provisional application No. 61/180,245, filed on May 21, 2009.

The present invention relates to methods and apparatus for non-contact sensing of articles with laser-based displacement sensors, in particular non-contact sensing of articles generally transparent to the laser wavelengths employed by the non-contact laser sensor. In more particular it relates to methods of determining the orientation of articles generally transparent to laser wavelengths by coating one surface of the article with material opaque to the wavelength of laser radiation used.

BACKGROUND

As laser processing becomes more capable and economical, more and more parts are being machined using laser processing rather than mechanical, chemical or electrical processing. One particular type of material that is adapting favorably to laser processing is glass and glass-like materials. Processing of glass or glass-like articles using a laser are discussed in two co-pending applications assigned to the assignee of this application, namely U.S. patent application Ser. No. 12/336,609 METHOD FOR LASER PROCESSING GLASS WITH A CHAMFERED EDGE and 61/164,162 GLASS MACHINING WITH PRECISELY TIMED LASER PULSES, both of which are included by reference.

During machining of glass articles, it's necessary to make sure that the correct side of the part to be machined is presented to the processing head. This is important since the machining operations are typically not symmetric with respect to the top and bottom of the article, therefore the article must be correctly oriented in order to be properly machined. This may not be trivial if the part in question has two or more sides that look sufficiently similar to make visual identification of the correct processing side difficult. An example is an essentially flat "sheet like" part that can be placed with either side up into the system. Typically, part manufacturers will try to ensure that there is no ambiguity as to which side of a part is the "processing side" by either marking this side with a unique identifier (such as a label, bar-code, etc.) which can be verified either by an operator or an automated machine vision system, or by drilling into the part fixturing holes that make it impossible to place the part in the processing area in any orientation other than the correct one.

Some articles, however, do not lend themselves to being oriented in this fashion. Marking or labeling the parts adds time and expense to the manufacturing process. Some articles do not lend themselves to adding part fixturing holes or features since they would detract from the finished product. A method of identifying which side of the part is uppermost is useful to prevent the article from being loaded improperly. In the case where the machine is loaded automatically without human intervention, a method of identifying the orientation of loaded articles can prevent the machine from processing the article on the wrong side.

There is therefore an ongoing need for a method and apparatus for identifying the orientation of a transparent article loaded into a laser processing machine.

SUMMARY OF THE INVENTION

An aspect of the instant invention relies upon the presence of an opaque coating applied to a portion of the transparent article for cosmetic purposes. This opaque coating one side of the article is detected and used to provide information regarding the orientation of the article. A conventional laser-based displacement detector is used to detect the opaque material on the transparent article to determine which side is uppermost in the machine. If the correct side is uppermost, processing proceeds. If it is determined that the incorrect side is uppermost, the article can be re-oriented automatically if the machine has that capability, or an operator can be alerted to re-orient the part. The applied opaque coating may remain after the machining operation if it is designed to be a cosmetic addition to the article or it may be removed following machining.

DETAILED DESCRIPTION OF PREFERRED EMBODIMENTS

Embodiments of this invention represent an improved method for processing a transparent article with a laser processing system having a controller. The invention includes applying a coating to one side of the transparent article and providing the laser processing system with a laser range measuring device. The embodiment then measures the location of the transparent article with the laser range measuring device by detecting the coating and communicating the location of the coating to the controller. The controller examines the reported location and decides whether or not to process said transparent article depending upon said location communicated to said controller.

Figure 1:
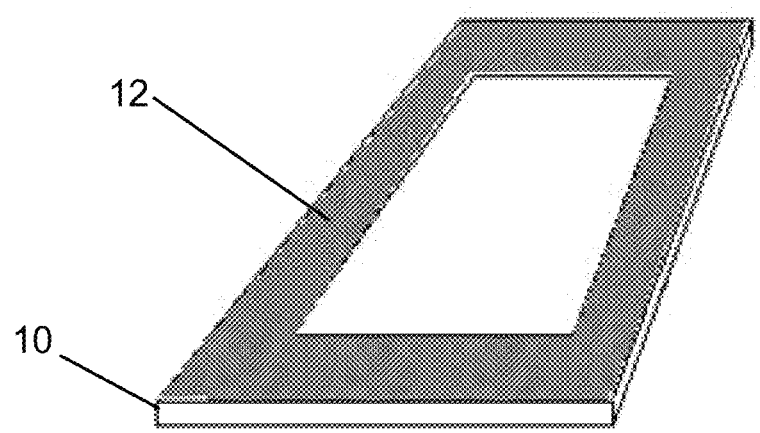
FIG. 1. A sample part.

This invention refers to establishing the correct processing side of a transparent article for machining purposes. Transparency in this case is defined principally as visual transparency to a human observer, however transparency with respect to the laser processing or measuring beam is also possible. An exemplary laser processing system for processing articles as described herein is the ESI Model MM5900 micro-machining system, manufactured by Electro Scientific Industries, Inc, Portland, Oreg. In a particular case, the material is clear glass, and the article is an essentially flat sheet with a band of black paint at the perimeter as shown in FIG. 1. FIG. 1 shows an article 10 with a coating 12 applied to the top surface of the article. Also in this case, it is important that the orientation is known since the machining operation is not symmetric with respect to the top and bottom surfaces of the article. In this embodiment a laser displacement sensor is used to detect the location of the article. An exemplary laser displacement sensor is the Acuity AR200 series sensor from Schmitt Industries, Portland, Oreg. 97210. Principles of operation of laser displacement sensors are well known and will not be discussed herein.

This sensor is selected so that the material to be located is transparent to the laser wavelength used. The coating applied to the article is selected to be opaque or at least partially reflective to the laser wavelength used. The laser sensor is directed to the article from a position above the article and perpendicular to the surface to be measured. The distance from the sensor to the article is measured and compared to predetermined distances stored in the controller of the laser processing system. By comparing the measured location of the reflective surface of the article, it can be determined whether the part has been inserted into the laser processing system right side up or upside down.

Figure 2A:
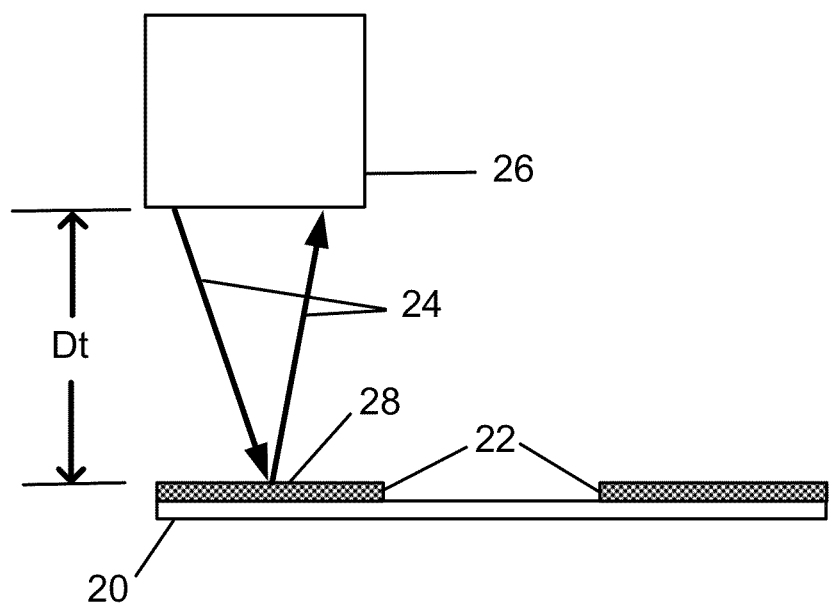
FIG. 2a. A sample part oriented paint side up.
Figure 2B:
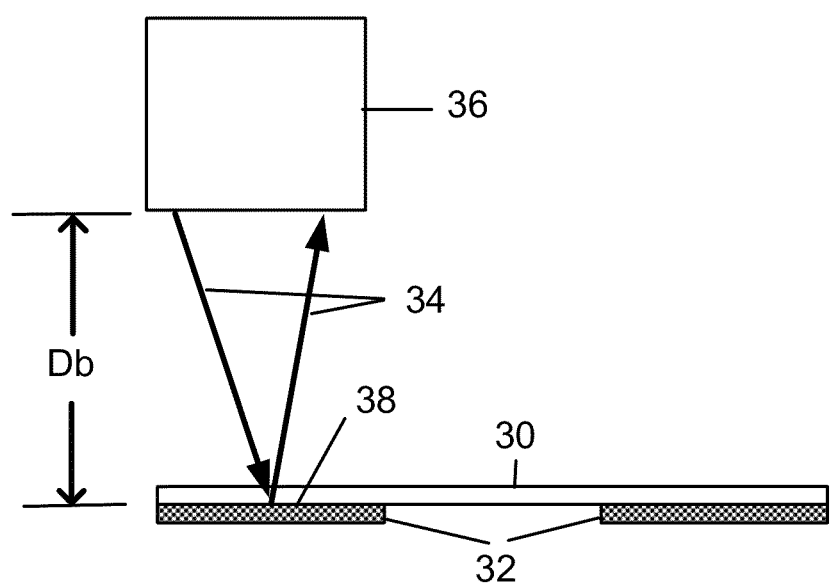
FIG. 2b. A sample part oriented paint side down.

FIG. 2a shows an article 20, loaded into a laser processing system (not shown) right side up with a coating 22 which is at least partially reflective to the laser radiation 24 emitted by the sensor 26, reflected off the top surface of the coating 28 and received by the sensor 26. This yields a value of Dt for the displacement of the article 20 from the sensor 26. FIG. 2b shows an article 30 loaded into a laser processing system (not shown) upside down with a coating 32 at least partially reflective to laser radiation 34 emitted by sensor 36, reflected off the bottom surface of the coating 38 and received by the sensor 36. This yields a measured displacement value of Db. Since Db is not approximately equal to the nominal value of Dt, the right side up measurement, the system concludes that the article has been inserted improperly. At this point the system can direct material handling elements of the system to turn the article over, if the embodiment of the invention is so equipped, or alert the operator that a part has been improperly inserted or simply stop.

In order to accomplish this, the laser sensor should be mounted in a position where it can report valid and repeatable locations for the measured part. This requires that the sensor be mounted in a known location so that the location can be reliably measured and communicated to the laser processing system controller. The sensor should be mounted so that the laser beam intersects the article as close to perpendicular as possible. The sensor should be mounted so that the laser beam will reflect off the coated portions of the article. In embodiments which have material handling elements, the article can be positioned by the material handling elements under the direction of the controller to direct the laser beam emitted by the laser sensor to impinge upon the coated portions of the article.

Coatings used by embodiments of this invention include paints, epoxies or powders that can be made to adhere to the glass or glass-like materials which comprise the articles to be laser machined. This adherence can be temporary, where the coating will be removed following machining, or permanent, where the coating forms a part of the cosmetic finish of the article. The coating can also be in the form of a film to be adhered to the article for the purpose of machining and removed following. This film could be made of plastic or paper for example. All of these embodiments are capable of adhering to an article made of glass or glass-like material and can reflect or partially reflect laser light at a wavelength to which the material is transparent or semi-transparent.

Determination of the orientation of the article depends upon a priori information programmed into the controller of the laser processing system. One manner of determining this is to insert an article correctly into the laser processing system and instruct the system to measure the article and store the results in the controller. An article which is subsequently incorrectly inserted into the system and measured will yield a measurement which differs from the stored value by the thickness of the transparent article. Once this data is acquired, the part orientation may be identified by comparing the acquired data with stored data with appropriate tolerances due to measurement error. For example, if the measured distance to the part inserted topside up is Dt and the measured distance to the part inserted bottom side up is Db, then a dual measurement threshold Td may be set $$Td=(Dt+Db)/2$$

Measurement less than or equal to Td indicate the part is correctly inserted. If, on the other hand, the perceived thickness, which is equal to t/n, where t is the thickness of the part and n the index or refraction of the material with respect to the laser wavelength is known, a single measurement threshold Ts may be calculated $$Ts=Dt+t/2n$$

Where a measurement less than Ts indicates the article is correctly inserted.

More elaborate algorithms can use the part distance measurements utilizing a sensor of the type described in this disclosure while still remaining within the scope of the approach outlined here. For this reason we request that the scope of this invention be determined solely by the following claims:

We claim:

1. A method for processing an article with a laser processing system having a controller, wherein the article has opposing first and second surfaces, wherein one of the first and second surfaces is a processing surface intended to be processed by the laser processing system, wherein the article has a coating applied to at least a region of one of the first or second surfaces, the method comprising:
   providing the laser processing system with a laser range measuring device, wherein the range measuring device utilizes a wavelength, wherein the article has a material that is transparent to the wavelength, and wherein the coating is reflective or partly reflective to the wavelength;
   directing laser light at the wavelength onto the applied coating;
   measuring a relative distance between the article and the laser range measuring device by employing the laser range measuring device to detect laser light reflected by the coating, wherein the relative distance is indicative of whether the first surface or the second surface is the processing surface;
   communicating the relative distance to the controller; and
   deciding whether or not to process the article depending upon the relative distance communicated to the controller.

2. The method of claim 1 wherein the laser range measuring device operates at a wavelength in the visible range.

3. The method of claim 1 wherein the laser processing system is a laser machining system.

4. The method of claim 1 wherein the material that is transparent to the wavelength comprises glass.

5. The method of claim 1 further, comprising:
   before the step of providing the laser processing system with a laser range measuring device, applying the coating to at least the region of one of the first or second surfaces.

6. The method of claim 1 wherein the first surface includes the region of the coating, and wherein the first surface is the processing surface.

7. The method of claim 1 wherein the step of deciding whether or not to process the article includes determining whether the relative distance to the coating is within a range of a predetermined acceptable distances stored in the controller.

8. The method of claim 1, wherein the first surface is the processing surface and the second surface is the nonprocessing surface, and wherein the step of deciding whether or not to process the article includes determining whether the processing surface is correctly oriented to be uppermost, the method further comprising:
   whenever the processing surface is uppermost, processing the article; and whenever the nonprocessing surface is uppermost, reorienting the article so that the processing surface is uppermost before processing the article.

9. The method of claim 1, wherein the region includes only a zone about a perimeter of one of the first and second surfaces.

10. The method of claim 1, wherein the coating is one of paint, epoxy, powder, or paper.

11. A method for determining an uppermost surface of an article, wherein the article has opposing processing and nonprocessing surfaces, wherein the processing surface is intended to be processed by a laser processing system, wherein the article has a coating applied to at least a region of one of the processing or nonprocessing surfaces, the method comprising:
inserting the article having the coating into a laser-processing system such that one of the processing or nonprocessing surfaces is uppermost;
directing laser light having a wavelength onto the coating; and
detecting laser light reflected by the coating, wherein the article has a material that is transparent to the wavelength, and wherein the coating is reflective or partly reflective to the wavelength; and
determining which one of the processing or nonprocessing surfaces is uppermost within the laser-processing system based on the detected laser light reflected by the coating.

12. The method of claim 11, wherein the coating comprises one of paint or epoxy.

13. The method of claim 11, wherein the coating is cosmetic.

14. The method of claim 11, wherein the coating comprises powder.

15. The method of claim 11, wherein the coating comprises paper.

16. The method of claim 11, further comprising:
whenever the processing surface is uppermost, processing the article; and
whenever the nonprocessing surface is uppermost, reorienting the article so that the processing surface is uppermost before processing the article.

17. A method for determining an uppermost surface of an article, wherein the article has opposing processing and nonprocessing surfaces, wherein the processing surface is intended to be processed by a processing system, wherein the article has a coating applied to at least a region of one of processing or nonprocessing surfaces, the method comprising:
inserting the article having the coating into the processing system such that one of the processing or nonprocessing surfaces is uppermost, wherein the processing system has a sensor;
determining a distance between the sensor and the coating applied to the article inserted within the processing system, wherein the distance is indicative of whether the processing surface or the nonprocessing surface is uppermost;
reorienting the article so that the processing surface is uppermost whenever the distance is indicative that the nonprocessing surface is uppermost; and
processing the article whenever the distance is indicative that the processing surface is uppermost.

18. The method of claim 17 wherein determining the distance comprises:
directing laser light at a wavelength onto the coating, wherein the sensor utilizes the wavelength, wherein the article has a material that is transparent to the wavelength, and wherein the coating is reflective or partly reflective to the wavelength; and
at the sensor, detecting laser light reflected by the coating.

19. The method of claim 17, wherein the processing system is a laser-processing system.

20. The method of claim 17, wherein the material is glass; wherein the coating is one of paint, epoxy, powder, or paper; and wherein the coating is applied to only a portion of the processing surface.

* * * * *